US006281215B1

(12) United States Patent
Moinet et al.

(10) Patent No.: US 6,281,215 B1
(45) Date of Patent: Aug. 28, 2001

(54) 4-(1-PIPERAZINYL) BENZOIC ACID DERIVATIVES, PROCESS FOR PREPARING THEM AND THEIR THERAPEUTIC APPLICATIONS

(75) Inventors: Gérard Moinet, Orsay; Gérard Botton, Buc; Liliane Doare, Chatillon; Micheline Kergoat, Bures-sur-Yvette; Didier Messangeau, Combs la Ville, all of (FR)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/331,155

(22) PCT Filed: Dec. 15, 1997

(86) PCT No.: PCT/EP97/07046

§ 371 Date: Oct. 20, 1999

§ 102(e) Date: Oct. 20, 1999

(87) PCT Pub. No.: WO98/27078

PCT Pub. Date: Jun. 25, 1998

(30) Foreign Application Priority Data

Dec. 18, 1996 (FR) .................................................. 96/15588

(51) Int. Cl.[7] ...................... A61K 31/495; C07D 295/15; C07D 295/155

(52) U.S. Cl. .................................. 514/253.06; 514/254.1; 514/255.03; 544/363; 544/379; 544/393

(58) Field of Search ...................................... 544/363, 379, 544/393; 514/253.06, 254.1, 255.03

(56) References Cited

U.S. PATENT DOCUMENTS

| 4,616,086 | * | 10/1986 | Witte et al. | 544/383 |
|---|---|---|---|---|
| 5,420,278 | * | 5/1995 | Cliffe | 544/392 |
| 5,492,912 | | 2/1996 | Godfroid et al. | 514/252 |
| 5,637,701 | * | 6/1997 | Ashwell | 540/597 |

FOREIGN PATENT DOCUMENTS

| 850 709 | 5/1977 | (BE) . |
|---|---|---|
| 2140229 | 1/1994 | (CA) . |
| 0638568 | 2/1995 | (EP) . |
| 2693722 | 1/1994 | (FR) . |
| 9626294 | 8/1996 | (WO) . |

* cited by examiner

Primary Examiner—Richard L. Raymond
(74) Attorney, Agent, or Firm—Millen White Zelano & Branigan

(57) ABSTRACT

New 4-(1-piperazinyl)benzoic acid derivatives of the formula (I) are described. Also described is methods for making these compounds and their use as therapeutic agents. In particular, the compounds find use in the treatment of diabetes.

9 Claims, No Drawings

4-(1-PIPERAZINYL) BENZOIC ACID DERIVATIVES, PROCESS FOR PREPARING THEM AND THEIR THERAPEUTIC APPLICATIONS

This application is a 371 of PCT/EP97/07046, filed Dec. 15, 1997.

The present invention relates to new 4-(1-pipera-zinyl) benzoic acid derivatives which are useful in the treatment of diabetes.

The subject of the present invention is thus compounds of general formula (I):

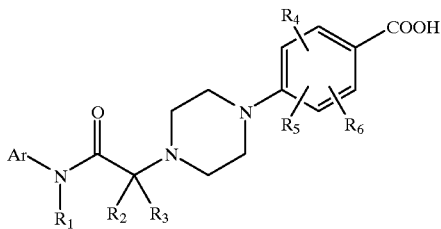

in which:

Ar is selected from a mono-, bi- or tricyclic aryl group having from 6 to 14 carbon atoms, a heteroaromatic group selected from the pyridyl, pyrimidyl, pyrrolyl, furyl, thienyl, quinolyl, indolyl, benzothienyl, benzofuryl, benzopyrranyl, benzothiopyrannyl, dibenzofuryl, carbazolyl and benzothiazinyl groups, it being possible for the Ar group to carry 1 to 3 substituents selected from a $C_1-C_8$ alkyl, $(C_3-C_8)$cycloalkyl $(C_1-C_6)$alkyl, $C_1-C_8$ alkoxy, $(C_3-C_8)$cycloalkyloxy $(C_1-C_6)$alkyl, $(C_3-C_8)$cycloalkyl $(C_1-C_6)$alkoxy $(C_1-C_6)$alkyl, $(C_3-C_8)$cycloalkyloxy $(C_3-C_8)$cycloalkyl $(C_1-C_6)$alkoxy, $(C_1-C_6)$alkoxy $(C_1-C_6)$alkyl, $C_6-C_{14}$ aryl, $C_6-C_{14}$ heteroaryl, $(C_6-C_{14})$heteroaryl $(C_1-C_6)$alkyl, $(C_6-C_{14})$aryl $(C_1-C_6)$alkyl, $(C_6-C_{14})$aryl $(C_1-C_6)$alkyl $(C_6-C_{14})$aryl, $(C_6-C_{14})$aryloxy, $(C_6-C_{14})$aryloxy $(C_1-C_6)$alkyl, $(C_6-C_{14})$aryl $(C_1-C_6)$alkyloxy or $(C_6-C_{14})$aryl $(C_1-C_6)$alkyloxy $(C_1-C_6)$alkyl group, a halogen, a trifluoromethyl, trifluoromethoxy, cyano, hydroxyl, nitro, amino, carboxyl, $(C_1-C_6)$alkoxycarbonyl, carbamoyl, $(C_1-C_8)$alkylthio, $(C_1-C_8)$alkylsulphinyl, $(C_1-C_8)$alkylsulphonyl, sulphoamino, $(C_1-C_8)$alkylsulphonylamino, sulphamoyl or $(C_1-C_8)$alkylcarbonylamino group, or two of these substituents forming a methylenedioxy group.

$R_1$, $R_2$ and $R_3$ are selected, independently of each other, from:

a hydrogen atom, a $C_1-C_8$ alkyl or $(C_1-C_6)$alkoxy $(C_1-C_6)$alkyl group, a cycloalkyl group containing from 3 to 8 carbon atoms, a $(C_3-C_8)$cycloalkyl $(C_1-C_6)$alkyl group, a $(C_3-C_8)$cycloalkyloxy $(C_1-C_6)$alkyl or $(C_3-C_8)$cycloalkyl $(C_1-C_6)$-alkoxy $(C_1-C_6)$alkyl group, a $C_6-C_{14}$ aryl, $C_6-C_{14}$ heteroaryl, $(C_6-C_{14})$heteroaryl $(C_1-C_6)$alkyl, $(C_6-C_{14})$aryl $(C_1-C_6)$alkyl $(C_6-C_{14})$aryl, $(C_6-C_{14})$aryl $(C_1-C_6)$alkoxy $(C_6-C3_4)$aryl, $(C_6-C_{14})$aryl $(C_1-C_6)$alkoxy $(C_1-C_6)$alkyl or $(C_6-C_{14})$aryloxy $(C_1-C_6)$alkyl group, or alternatively $R_1$ forms with the nitrogen atom to which $R_1$ is attached and the Ar group a ring selected from indolinyl, quinolyl, indolyl and tetrahydroquinolyl, $R_4$, $R_5$, $R_6$ are selected, independently of each other, from:

a hydrogen atom, a $C_1-C_8$ alkyl, $(C_3-C_8)$cycloalkyl $(C_1-C_6)$alkyl, $C_1-C_8$ alkoxy, $(C_3-C_8)$cycloalkyloxy $(C_1-C_6)$alkyl, $(C_3-C_8)$cycloalkyloxy, $(C_3-C_8)$cycloalkyl $(C_1-C_6)$alkoxy, $(C_3-C_8)$cycloalkyl $(C_1-C_6)$alkoxy $(C_1-C_6)$alkyl, $(C_1-C_6)$alkoxy $(C_1-C_6)$alkyl, $C_6-C_{14}$ aryl, $(C_6-C_{14})$ aryl $(C_1-C_6)$alkyl, $(C_6-C_{14})$aryl $(C_1-C_6)$alkyl $(C_6-C_{14})$aryl, $(C_6-C_{14})$aryloxy, $(C_6-C_{14})$aryloxy $(C_1-C_6)$alkyl, $(C_1-C_{14})$aryl $(C_1-C_6)$alkoxy or $(C_6-C_{14})$aryl $(C_1-C_6)$alkyloxy $(C_1-C_6)$alkyl group, a halogen, a trifluoromethyl, trifluoromethoxy, cyano, carboxyl, hydroxyl, nitro, amino, $(C_1-C_6)$alkoxycarbonyl, carbamoyl, $(C_1-C_8)$alkylthio, $(C_1-C_8)$alkylsulphinyl, $(C_1-C_8)$alkylsulphonyl, sulphoamino, $(C_1-C_8)$alkylsulphonylamino, sulphamoyl or $(C_1-C_8)$alkylcarbonylamino group, it being possible for two of these groups to form a methylenedioxy group, it being possible for the various aryl groups themselves to be substituted with 1 to 3 substituents selected from a $C_1-C_8$ alkyl or $C_1-C_8$ alkoxy group, a halogen, a trifluoromethyl, trifluoromethoxy, hydroxyl, nitro and amino group, their solvates and their pharmaceutically acceptable salts.

As an example of an aryl group, there may be mentioned the phenyl, α-naphthyl, β-naphthyl and fluorenyl groups.

The $C_1-C_8$ alkyl groups may be linear or branched. As examples, there may be mentioned the methyl, ethyl, propyl, isopropyl, butyl, isobutyl, tert-butyl and pentyl groups.

The $C_1-C_8$ alkoxy groups may likewise be linear or branched. As examples, there may be mentioned the methoxy, ethoxy, propoxy, isopropoxy, butoxy and isobutoxy groups.

The halogens may be selected from fluorine, chlorine, bromine and iodine.

The invention also relates to the tautomeric, enantiomeric, diasterecisomeric and epimeric forms of the compounds of general formula (I).

The compounds of general formula (I) have a carboxylic acid functional group and may be salified, they then being in the form of salts with bases.

Examples of salts with bases of the compounds of general formula (I) include the pharmaceutically acceptable salts such as the sodium salts, potassium salts, calcium salts and other salts of the same type.

The compounds of general formula (I) can also be salified with amines in order to form pharmaceutically acceptable salts. By way of example, it will be possible for the compounds of general formula (I) to be salified with glucanine, N-methylglucamine, N,N-dimethylglucamine, ethanolamine, morpholine, N-methylmorpholine or lysine.

The compounds of general formula (I) possess basic nitrogen atoms and can be monosalified or disalified with inorganic or organic acids. Examples of salts with acids of the compounds of general formula (I) include the pharmaceutically acceptable salts such as, and non-exhaustively, hydrochloride, hydrobromide, sulphate, succinate, maleate, fumarate, malate, tartrate and sulphonates such as methanesulphonate, benzenesulphonate and toluenesulphonate.

Among the compounds of general formula (I) according to the invention, there may be mentioned more particularly, as preferred compound, 4-{4-[2(N-isopropyl-N-phenylamino)-2-oxoethyl]-1-piperazinyl}benzoic acid, 4-{4-[2-(N-[2,6-dimethylphenyl]amino)-2-oxoethyl]-1-piperazinyl}benzoic acid and 4-{4-2-(N-[2,6-diisopropylphenyl]amino-2-oxoethyl]-1-piperazinyl}benzoic acid.

The invention also relates to a process for the preparation of the compounds of general formula (I). A process of preparation according to the invention comprises reactimg an aromatic amine of general formula (II):

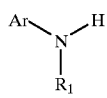

(II)

in which Ar and $R_1$ are as defined above, with a haloacyl halide of general formula (III):

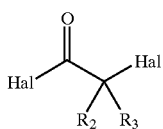

(III)

in which Hal represents a chlorine or bromine atom, $R_2$ and $R_3$ are defined above, in order to form a compound of general formula (IV):

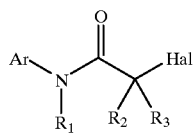

(IV)

in which Ar, $R_1$, $R_2$, $R_3$ and Hal are as defined above, and reacting the compound of general formula (IV) with a compound of general formula (V):

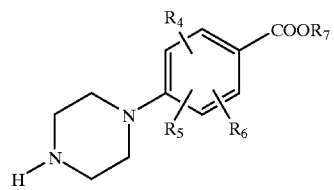

(V)

in which $R_4$, $R_5$ and $R_6$ are as defined above and $R_7$ is a hydrogen atom or a $C_1$–$C_6$ alkyl group, in the presence of a basic agent such as triethylamine in order to form the compound of general formula (VI):

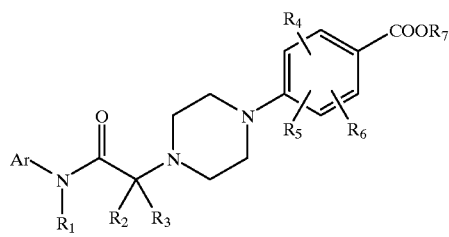

(VI)

in which Ar, $R_1$, $R_2$, $R_3$, $R_4$, $R_5$, $R_6$ and $R_7$ are as defined above.

In the case where $R_7$ is an alkyl group, the compound of general formula (VI) can be hydrolyzed by conventional acidic or basic means in order to give the compound of general formula (I):

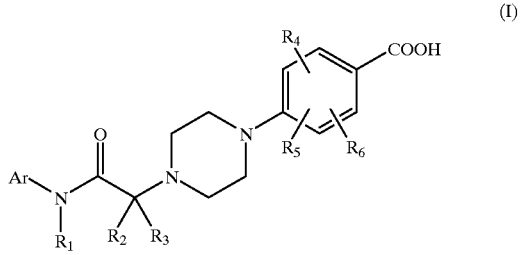

(I)

in which Ar, $R_1$, $R_2$, $R_3$, $R_4$, $R_5$ and $R_6$ are as defined above.

The compounds of formula (V) are known compounds. They can be synthesized according to the procedure described by V. Prelog and Z. Blazek in Collection Czechoslov. Chem. Communications 6, 211–24 (1934) for ethyl 4-(1-piperazinyl)benzote.

By way of example, the compound (VI), in which R is an alkyl group, can be hydrolyzed in the presence of a basic agent such as dilute sodium hydroxide.

The enantiomers of the compounds of formula (I) can be separated by successive recrystallization of the salt of the acid (I) with an optically active base from solvents such as acetone, ethyl acetate or isopropanol, followed by displacement from the salt into an optically active acid by an inorganic or organic acid, according to a conventional method.

The compounds according to the present invention can be used in the treatment of diabetes, in particular of non-insulin-dependent diabetes because of their hypoglycaemic effect and of their lack of toxicity at the active doses.

The subject of the present invention is therefore also pharmaceutical compositions comprising, as active ingredient, a compound according to the invention.

The pharmaceutical compositions according to the invention can be provided in forms intended for administration by the parenteral, oral, rectal, permucosal or percutaneous route.

They can therefore be provided in the form of injectable solutions or suspensions or in multidose vials, in the form of plain or coated tablets, sugarcoated tablets, capsules, gelatin capsules, pills, cachets, powders, suppositories or rectal capsules, of solutions or suspensions, for percutaneous use in a polar solvent, for permucosal use.

The excipients which are suitable for such administrations are cellulose derivatives or microcrystalline cellulose, alkaline-earth metal carbonates, magnesium phosphate, starches, modified starches, and lactose for the solid forms.

For rectal use, cocoa butter or polyethylene glycol stearates are the preferred excipients.

For parenteral use, water, aqueous solutions, physiological saline or isotonic solutions are the vehicles most conveniently used.

The dosage may vary within wide limits depending on the therapeutic indication and the route of administration, as well as the age and weight of the subject.

The following examples illustrate the preparation of the compounds of formula I.

EXAMPLE 1

Preparation of 4-{4-[2-(4-chlorophenylamino)-2-oxoethyl]-1-piperazinyl}benzoic acid (Compound No. 5).

A—Preparation of 2-chloro-N-(4-chlorophenyl)-acetamide 34.5 ml of chloroacetyl chloride are added dropwise to 50 g of 4-chloroaniline and 108 g of potassium carbonate in 400 ml of chloroform.

The reaction medium is then filtered and the solid obtained is taken up in 1500 ml of water. After stirring for 1 h, the solid in suspension is filtered and thoroughly washed with water.

70.5 g of 2-chloro-N-(4-chlorophenyl)acetamide are thus obtained in the form of a white solid whose melting point is 169–170° C.

IR (KBr): 1669 cm$^{-1}$ (C=O amide); $^1$H NMR: (DMSO-d$_6$, 200 MHz) δ ppm 4.25 (2H, s, CH2), 7.30 (2H, d, phenyl protons), 7.60 (2H, d, phenyl protons), 10.40 (1H, s, NH).

B—Preparation of the ethyl ester of 4-{4-[2-(4-chlorophenylamo)-2-oxoethyl]-1-piperazinyl}benzoic acid 25 g of 2-chloro-N-(4-chlorophenyl)acetamide, 35.2 g of ethyl 4-(1-piperazinyl)benzoate and 80 g of potassium carbonate in 300 ml of DMF are reacted over-night at room temperature, with stirring.

The reaction medium is filtered in order to separate the insoluble matter and the filtrate thus obtained is poured over 1000 ml of water. A solid crystallizes. This solid is filtered and washed with water in order to give 39 g of the ethyl ester of 4-{4-[2chlorophenylamino)-2-oxoethyl]-1-piperazinyl}benzoic acid in the form of a solid whose melting point is 172–174° C.

IR (KBr): 1686 cm$^{-1}$, (C=O ester) $^1$H NMR: (DMSO-d$_6$, 200 MHz) δ ppm 1.20 (3H, t, CH$_3$), 2.50 (4H, s, 2CH$_2$), 3.05 (2H, s, CH$_2$), 3.20 δ54H, s, 2CH$_2$), 4.05 (2H, q, CH$_2$), 6.80 (2H, d, phenyl protons), 7.20 (2H, d, phenyl protons), 7.60 (4H, m, phenyl protons), 9.80 (1H, s, NH).

C—Preparation of 4-{4-[2-(4-chlorophenylamino)-2-oxoethyl]-1-liperazinyl]benzoic acid 20 g of the ethyl ester of 4-{4-[2-(4-chlorophen-ylamino)-2-oxoethyl]-1-piperazinyl}benzoic acid, 165 ml of a 1 N aqueous sodium hydroxide solution and 150 ml of ethanol are heated under reflux, with stirring, for 1 h.

The mixture is acidified with concentrated hydrochloric acid to pH 5. A solid crystallizes. This solid is filtered and washed with ethanol in order to give 16.4 g of the desired crude product. Recrystallization, in a DMF/acetonitrile (1/1) mixture, gives 13.6 g of 4-{4-[2-(4-chlorophenylamino)-2-oxoethyl]-1-piperazinyl}benzoic acid in the form of a white solid which melts at 263–265° C.

IR (KBr): 1676 cm$^{-1}$ (C=O acid); $^1$H NMR: (DMSO-d$_6$, 200 MHz) δ ppm 2.7 (4H, s, 2CH$_2$) 3.20 (2H, s, CH$_2$) 3.40 (4H, s, 2CH$_2$) 7.0 (2H, d, phenyl protons), 7.40 (2H, d, phenyl protons) 7.75 (4H, m, phenyl protons), 9.90 (1H, s, NH), 12.40 (1H, broad s, acidic OH).

The formulae and characteristics of the compounds according to the invention are assembled in Table 1 below.

TABLE 1

| Compound No. | Structure | m.p. in ° C. (Kofler) | $^1$H NMR (200 MHz) δ ppm |
|---|---|---|---|
| 1 | (structure with CH$_3$, NH, piperazine, COOH) | 199–201 | DMSO-d6<br>2.16(s, 6H)<br>2.75(s, 4H)<br>3.22(s, 2H)<br>3.45(s, 4H)<br>7.0+7.1(d+s, 5H)<br>7.83(d, 2H)<br>9.32(s, 1H)<br>12.38(s, 1H) |
| 2 | (structure with N-benzyl, phenyl, piperazine, COOH) | 188–190 | DMSO-d6<br>2.50(s, 4H)<br>3.08(s, 2H)<br>3.28(s, 4H)<br>4.87(s, 2H)<br>6.90(d, 2H)<br>7.25(m, 10H)<br>7.77(d, 2H)<br>12.32(s, 1H) |
| 3 | (structure with N-isopropyl, phenyl, piperazine, COOH) | 229–231 | DMSO-d6<br>1.0(d, 6H)<br>2.40(s, 4H)<br>2.75(s, 2H)<br>3.25(s, 4H)<br>4.82(m, 1H)<br>6.90(d, 2H)<br>7.25(d, 2H)<br>7.50(s, 3H)<br>7.80(d, 2H)<br>12.35(s, 1H) |

TABLE 1-continued

| Compound No. | Structure | m.p. in °C. (Köfler) | ¹H NMR (200 MHz) δ ppm |
|---|---|---|---|
| 4 | 2,6-diisopropylphenyl-NH-C(O)-CH₂-piperazine-C₆H₄-COOH | 239–241 | DMSO-d6<br>1.1(d, 12H)<br>2.7(s, 4H)<br>3.05(m, 2H)<br>3.25(s, 2H)<br>3.40(s, 4H)<br>5.95(d, 2H)<br>7.2(m, 3H)<br>7.8(d, 2H)<br>9.3(s, 1H)<br>12.4(s, 1H) |
| 5 | 4-Cl-C₆H₄-NH-C(O)-CH₂-piperazine-C₆H₄-COOH | 263–265 | DMSO-d6<br>2.70(s, 4H)<br>3.20(s, 2H)<br>3.40(s, 4H)<br>7.00(d, 2H)<br>7.40((d, 2H)<br>7.75(m, 4H)<br>9.90(s, 1H)<br>12.4(s, 1H) |
| 6 | 5-Cl-2-OCH₃-C₆H₃-NH-C(O)-CH₂-piperazine-C₆H₄-COOH | >265 | CF3COOD<br>3.65(s, 3H)<br>4.20(s, 6H)<br>4.55(s, 2H)<br>6.80(d, 1H)<br>7(d, 1H)<br>7.60(d, 3H)<br>8.25(d, 2H) |
| 7 | C₆H₅-N(CH₃)-C(O)-CH₂-piperazine-C₆H₄-COOH | 205–207 | CF3COOD<br>3.20(s, 3H)<br>3.95(m, 10H)<br>6.90(s, 2H)<br>7.20(s, 3H)<br>7.50(d, 2H)<br>8.10(d, 2H) |
| 8 | 3-CF₃-C₆H₄-NH-C(O)-CH₂-piperazine-C₆H₄-COOH | 259–261 | CF3COOD<br>4.15(s, 6H)<br>4.45(s, 2H)<br>7.32(s, 3H)<br>7.50(m, 3H)<br>8.10(d, 2H) |
| 9 | 4-F-C₆H₄-NH-C(O)-CH₂-piperazine-C₆H₄-COOH | 263–265 | CF3COOD<br>4.25(s, 8H)<br>4.55(s, 2H)<br>7.00(s, 2H)<br>7.25(s, 2H)<br>7.70(d, 2H)<br>8.30(d, 2H) |

TABLE 1-continued

| Compound No. | Structure | m.p. in °C. (Köfler) | ¹H NMR (200 MHz) δ ppm |
|---|---|---|---|
| 10 | 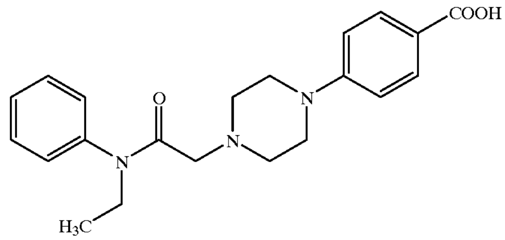 | 201–203 | CF3COOD<br>1.12(t, 3H)<br>3.75(q, 2H)<br>4.38(m, 10H)<br>7.13(d, 2H)<br>7.45(s, 3H)<br>7.67(d, 2H)<br>8.28(d, 2H) |
| 11 | 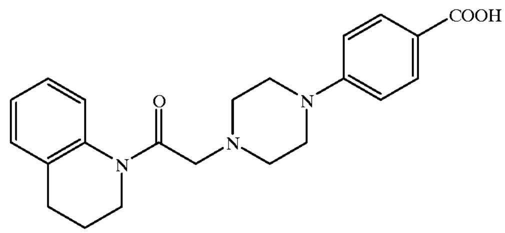 | 226–228 | CF3COOD<br>1.94(s, 2H)<br>2.54(s, 2H)<br>4.19(m, 12H)<br>7.12(m, 4H)<br>7.70(d, 2H)<br>8.28(s, 2H) |
| 12 | 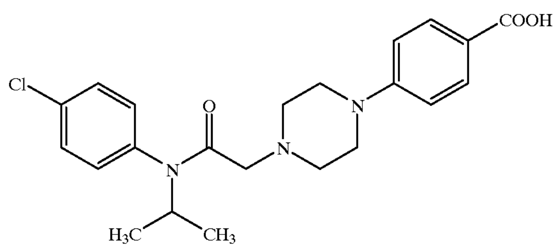 | 252–254 | CF3COOD<br>1.11(s, 6H)<br>4.03+4.20(s+s, 8H)<br>4.49(s, 2H)<br>4.85(s, 1H)<br>7.13(s, 2H)<br>7.48(s, 2H)<br>7.74(s, 2H)<br>8.34(s, 2H) |
| 13 | 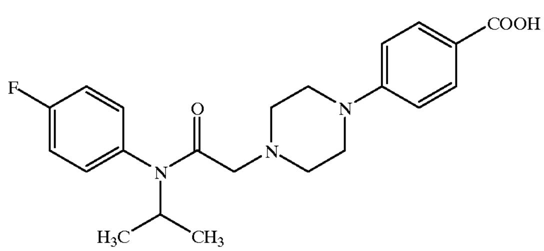 | 233–235 | CF3COOD<br>1.05(s, 6H)<br>3.80+4.30(s+s, 10H)<br>4.75(s, 1H)<br>7.05(s, 4H)<br>7.60(s, 2H)<br>8.25(s, 2H) |
| 14 | 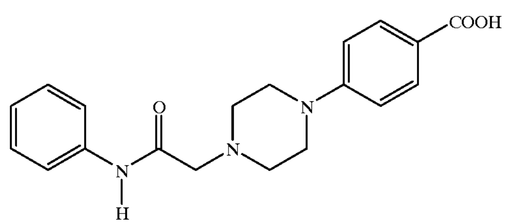 | 257–259 | CF3COOD<br>4.25(s, 8H)<br>4.5(s, 2H)<br>7.25(s+m, 5H)<br>7.89(d, 2H)<br>8.29(d, 2H) |
| 15 | 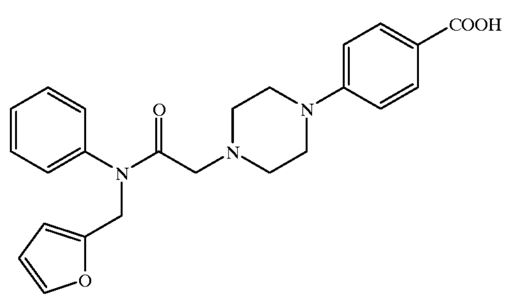 | 163–165 | CF3COOD<br>2.28(s, 4H)<br>2.72(s, 2H)<br>2.97(s, 4H)<br>4.62(s, 2H)<br>5.94(s, 1H)<br>6.10(s, 1H)<br>6.70(d, 2H)<br>6.95(d, 2H)<br>7.13(d, 3H)<br>7.33(s, 1H)<br>7.55(d, 2H)<br>12.10(s, 1H) |

TABLE 1-continued

| Compound No. | Structure | m.p. in °C. (Köfler) | $^1$H NMR (200 MHz) δ ppm |
|---|---|---|---|
| 16 | H₃C–C₆H₄–NH–C(O)–CH₂–N(piperazine)N–C₆H₄–COOH | 259–261 | CF3COOD<br>2.29(s, 3H)<br>4.34(s, 5H)<br>4.80(s, 2H)<br>7.18(s+m, 4H)<br>7.77(d, 2H)<br>8.38(d, 2H) |
| 17 | H₃CO–C₆H₄–NH–C(O)–CH₂–N(piperazine)N–C₆H₄–COOH | 245–247 | CF3COOD<br>3.88(s, 3H)<br>4.29(s, 8H)<br>4.57(s, 2H)<br>6.98(d, 2H)<br>7.28(d, 2H)<br>7.73(d, 2H)<br>8.33(d, 2H) |
| 18 | Ph–N(cyclohexyl)–C(O)–CH₂–N(piperazine)N–C₆H₄–COOH | 208–210 | CF3COOD<br>1.18(m, 6H)<br>1.78(t, 4H)<br>3.97(s, 4H)<br>4.17(d, 4H)<br>4.45(d, 3H)<br>7.08(m, 2H)<br>7.47(d, 3H)<br>7.70(d, 2H)<br>8.30(d, 2H) |
| 19 | Cl–C₆H₄–N(CH₃)–C(O)–CH₂–N(piperazine)N–C₆H₄–COOH | 217–219 | CF3COOD<br>3.48(s, 3H)<br>4.27(m+s, 10H)<br>7.26(d, 2H)<br>7.55(d, 2H)<br>7.82(d, 2H)<br>8.43(d, 2H) |

Results of pharmacological studies will be given below.

Study of the Antidiabetic Activity in NOSTZ Rats

The antidiabetic activity of the compounds of formula I is determined by the oral route on an experimental model of non-insulin-dependent diabetes, induced in rats by streptozotocin.

The non-insulin-dependent diabetes model is obtained in rats by neonatal injection (on the day of birth) of streptozotozin.

The diabetic rats used are 8 weeks old. The animals are housed, from the day they are born to the day of the experiment, in an animal house at a regulated temperature of 21 to 22° C., and it is subjected to a fixed light (from 7 a.m. to 7 p.m.) and dark (from 7 p.m. to 7 a.m.) cycle. Their food consisted of a maintenance diet, water and food were provided "ad libitum", with the exception of the 2 hours fasting preceding the tests during which food is withdrawn (postabsorptive state).

The rats are treated by the oral route during the day with the test product. Two hours after the last administration of the product and 30 minutes after anaesthetizing the animals with sodium pentobarbital (Nembutal®), a 300 µl blood sample is collected at the end of the tail.

Table II assembles the principal results obtained. These results show the efficacy of the compounds of formula I in causing a decrease in glycaemia in the diabetic animals.

These results are expressed as a percentage variation in the glycaemia at D4 (4 days of treatment) compared with D0 (before treatment).

TABLE 2

| Compound | 20 mg/kg/d % Glycaemia at D4 | 20 mg/kg/d % Glycaemia at D4 |
|---|---|---|
| 1 | −6 | −16 |
| 2 | −2 | −10 |
| 3 | −13 | −22 |
| 4 | −8 | −16 |
| 5 | −9 | −12 |

What is claimed is:

1. A compound of the formula (I):

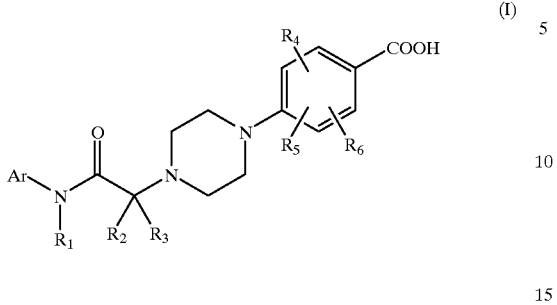

in which:

Ar is selected from
- a mono-, bi- or tricyclic aryl group having from 6 to 14 carbon atoms,
- a heteroaromatic group selected from the pyridyl, pyrimidyl, pyrrolyl, furyl, thienyl, quinolyl, indolyl, benzothienyl, benzofuryl, benzopyrranyl, benzothiopyrannyl, dibenzofuryl, carbazolyl and benzothiazinyl groups,
- optionally, the Ar group carrying 1 to 3 substituents selected from $C_1$–$C_8$ alkyl, $(C_3$–$C_8)$cyclo-alkyl $(C_1$–$C_6)$alkyl, $C_1$–$C_8$ alkoxy, $(C_3$–$C_8)$cycloalkyloxy $(C_1$–$C_6)$alkyl, $(C_3$–$C_8)$cycloalkyl $(C_1$–$C_6)$alkoxy $(C_1$–$C_6)$alkyl, $(C_3$–$C_8)$cycloalkyloxy, $(C_3$–$C_8)$cycloalkyl $(C_1$–$C_6)$alkoxy, $(C_1$–$C_6)$alkoxy $(C_1$–$C_6)$alkyl, $C_6$–$C_{14}$ aryl, $C_6$–$C_{14}$ heteroaryl, $(C_6$–$C_{14})$heteroaryl $(C_1$–$C_6)$alkyl, $(C_6$–$C_{14})$aryl $(C_1$–$C_6)$alkyl, $(C_6$–$C_{14})$aryl $(C_1$–$C_6)$alkyl $(C_6$–$C_{14})$aryl, $(C_6$–$C_{14})$aryloxy, $(C_6$–$C_{14})$aryloxy, $(C_1$–$C_6)$aryloxy $(C_1$–$C_6)$alkyl, $(C_6$–$C_4)$aryl $(C_1$–$C_6)$alkyloxy or $(C_6$–$C_{14})$aryl $(C_1$–$C_6)$alkyloxy $(C_1$–$C_6)$alkyl groups, a halogen, a trifluoromethyl, trifluoromethoxy, cyano, hydroxyl, nitro, amino, carboxyl, $(C_1$–$C_6)$alkoxycarbonyl, carbamoyl, $(C_1$–$C_8)$alkylthio, $(C_1$–$C_8)$alkylsulphinyl, $(C_1$–$C_8)$alkylsulphonyl, sulphoamino, $(C_1$–$C_8)$alkylsulphonylamino, sulphamoyl or $(C_1$–$C_8)$ alkylcarbonylamino group, or two substituents together forming a methylenedioxy group;

$R_1$, $R_2$ and $R_3$ are selected, independently of each other, from:
- a hydrogen atom,
- a $C_1$–$C_8$ alkyl or $(C_1$–$C_6)$alkoxy$(C_1$–$C_6)$alkyl group,
- a cycloalkyl group containing from 3 to 8 carbon atoms, a $(C_3$–$C_8)$cycloalkyl$(C_1$–$C_6)$ alkyl group, a $(C_3$–$C_8)$cycloalkyloxy$(C_1$–$C_6)$alkyl or $(C_3$–$C_8)$cycloalkyl$(C_1$–$C_6)$-alkoxy$(C_1$–$C_6)$alkyl group,
- a $C_6$–$C_{14}$aryl, $C_6$–$C_{14}$heteroaryl, $(C_6$–$C_{14})$heteroaryl $(C_1$–$C_6)$alkyl, $(C_6$–$C_{14})$aryl $(C_1$–$C_6)$alkyl $(C_6$–$C_{14})$aryl $(C_1$–$C_6)$alkyl $(C_6$–$C_{14})$aryl $(C_6$–$C_{14})$ aryl, $(C_1$–$C_6)$alkoxy $(C_1$–$C_6)$alkyl or $(C_6$–$C_{14})$ aryloxy $(C_1$–$C_6)$alkyl group,
- or alternatively $R_1$ forms with the nitrogen atom to which $R_1$ is attached and the Ar group a ring selected from indolinyl, quinolyl, indolyl and tetrahydroquinolyl; and $R_4$, $R_5$, $R_6$ are selected, independently of each other, from:
- a hydrogen atom,
- a $C_1$–$C_8$alkyl, $(C_3$–$C_8)$cycloalkyl $(C_1$–$C_6)$alkyl, $C_1$–$C_8$ alkoxy, $(C_3$–$C_8)$cycloalkyloxy $(C_6$–$C_6)$ alkyl, $(C_3$–$C_8)$cycloalkyl $(C_1$–$C_6)$alkoxy $(C_1$–$C_6)$ alkyl, $(C_3$–$C_8)$cycloalkyloxy, $(C_3$–$C_8)$cycloalkyl $(C_1$–$C_6)$alkoxy, $(C_1$–$C_6)$alkoxy $(C_1$–$C_6)$alkyl, $C_6$–$C_{14}$ aryl, $C_6$–$C_{14}$ heteroaryl, $(C_6$–$C_{14})$ heteroaryl $(C_1$–$C_6)$alkyl, $(C_6$–$C_{14})$aryl $(C_1$–$C_6)$ alkyl, $(C_6$–$C_{14})$aryl $(C_1$–$C_6)$alkyl $(C_6$–$C_{14})$aryl, $(C_6$–$C_{14})$aryloxy, $(C_6$–$C_{14})$aryloxy $(C_1$–$C_6)$alkyl, $(C_6$–$C_{14})$aryl $(C_1$–$C_6)$alkyloxy or $(C_6$–$C_{14})$aryl $(C_1$–$C_6)$alkyloxy $(C_1$–$C_6)$alkyl groups, a halogen, a trifluoromethyl, trifluoromethoxy, cyano, hydroxyl, nitro, amino, $(C_1$–$C_6)$alkoxycarbonyl, carbamoyl, $(C_1$–$C_8)$alkylthio, $(C_1$–$C_8)$ alkylsulphinyl, $(C_1$–$C_8)$alkylsulphonyl, sulphoamino, $(C_1$–$C_8)$alkylsulphonylamino, sulphamoyl or $(C_1$–$C_8)$alkylcarbonylamino group,
- optionally two of the $R_4$, $R_5$ and $R_6$ groups together form a methylenedioxy group, and
- optionally, each aryl group being substituted with 1 to 3 substituents selected from a $C_1$–$C_8$ alkyl or $C_1$–$C_8$ alkoxy group, a halogen, a trifluoromethyl, trifluoromethoxy, hydroxyl, nitro and amino group,
- wherein heteroaryl in each case is selected from the pyridyl, pyrimidyl, pyrrolyl, furyl, thienyl, quinolyl, indolyl, benzothienyl, benzofuryl, benzopyrranyl, benzothiopyrannyl, dibenzofuryl, carbazolyl and benzothiazinyl groups;

solvates thereof and pharmaceutically acceptable salts thereof.

2. A compound of claim 1, wherein Ar is phenyl, α-naphthyl, β-naphthyl or fluorenyl.

3. A compound of claim 1, wherein Ar is phenyl, α-naphthyl, β-naphthyl or fluorenyl, optionally carrying 1 to 3 of the substituents defined in claim 1.

4. A compound which is 4-{4-[2(N-isopropyl-N-phenylamino)-2-oxoethyl]-1-piperazinyl}-benzoic acid, 4-{4-[2-(N-[2,6-dimethylphenyl]amino)-2-oxoethyl]-1-piperazinyl}benzoic acid or 4-{4-[2-(N-[2,6-diisopropylphenyl]amino)-2-oxoethyl]-1-piperazinyl}benzoic acid.

5. A process for preparing a compound according to claim 1, comprising reacting an aromatic amine of formula (II):

in which Ar and $R_1$ are as defined with a haloacyl halide of formula (III):

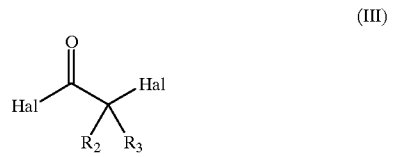

in which Hal represents a chlorine or bromine atom, where $R_2$ and $R_3$ are as defined in order to form a compound of formula (IV):

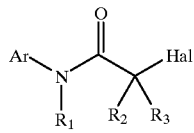

(IV)

in which Ar, $R_1$, $R_2$, $R_3$ and Hal are as defined, and reacting the compound of formula (IV) with a compound of formula (V):

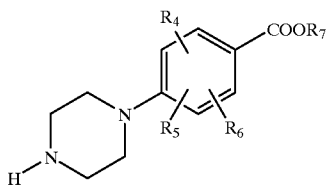

(V)

in which $R_4$, $R_5$ and $R_6$ are as defined and $R_7$ is a hydrogen atom or a $C_1$–$C_6$ alkyl group, in the presence of a basic agent to form the compound of formula (VI):

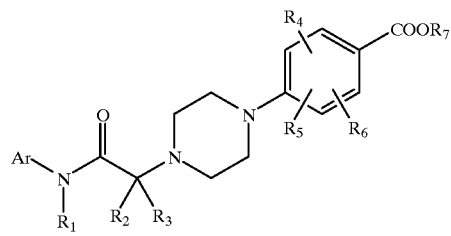

(VI)

in which Ar, $R_1$, $R_2$, $R_3$, $R_4$, $R_5$, $R_6$ and $R_7$ are as defined, and in the case where $R_7$ is an alkyl group, hydrolyzing this compound in order to form a compound of formula (I).

6. The process of claim 5, wherein the basic agent is triethylamine.

7. A pharmaceutical composition comprising, as active ingredient, a compound according to claim 1.

8. A pharmaceutical composition comprising, as active ingredient, a compound according to claim 4.

9. A method for the treatment of diabetes which comprises administering to a patient in need thereof an effective amount of a compound of claim 1.

* * * * *

UNITED STATES PATENT AND TRADEMARK OFFICE
CERTIFICATE OF CORRECTION

PATENT NO. : 6,281,215 B1
DATED : August 28, 2001
INVENTOR(S) : Moinet et al.

It is certified that error appears in the above-identified patent and that said Letters Patent is hereby corrected as shown below:

Column 13,
Line 38, reads "aryloxy, $(C_6-C_{14})$ aryloxy, $(C_1-C_6)$arloxy $(C_1-C_6)$" should read
-- aryloxy, $(C_6-C_{14})$aryloxy $(C_1-C_6)$ --

Line 39, reads "alkyl, $(C_6-C_4)$aryl $(C_1-C_6)$alkyloxy or $(C_6-C_{14})$aryl" should read
-- alkyl, $(C_6-C_{14})$aryl $(C_1-C_6)$alkyloxy or $(C_6-C_{14})$aryl --

Line 59, reads "$(C_1-C_6)$alkyl, $(C_6-C_{14})$aryl $(C_1-C_6)$alkyl" should read
-- $(C_1-C_6)$alkyl, $(C_6-C_{14})$aryl $(C_1-C_6)$alkyl, --

Line 60, reads "$(C_6-C_{14})$aryl $(C_1-C_6)$alkyl $(C_6-C_{14})$aryl $(C_6-C_{14})$" should read
-- $(C_6-C_{14})$aryl $(C_1-C_6)$alkyl $(C_6-C_{14})$aryl, $(C_6-C_{14})$--

Line 61, reads "aryl, $(C_1-C_6)$" should read -- aryl $(C_1-C_6)$ --

Column 14,
Line 5, reads "$(C_6-C_6)$" should read -- $(C_1-C_6)$ --

Line 9, reads "$C_6-C_{14}$ aryl, $C_6-C_{14}$ heteroaryl, $(C_6-C_{14})$" should read
-- $(C_6-C_{14})$ aryl, $(C_6-C_{14})$ heteroaryl, $(C_6-C_{14})$ --

Signed and Sealed this

Second Day of April, 2002

Attest:

*Attesting Officer*

JAMES E. ROGAN
*Director of the United States Patent and Trademark Office*